(12) United States Patent
Archibald

(10) Patent No.: US 12,048,777 B2
(45) Date of Patent: *Jul. 30, 2024

(54) DEVICES AND METHODS FOR NERVE REGENERATION

(71) Applicant: Integra LifeSciences Corporation, Princeton, NJ (US)

(72) Inventor: Simon J. Archibald, Pennington, NJ (US)

(73) Assignee: Integra LifeSciences Corporation, Princeton, NJ (US)

(*) Notice: Subject to any disclaimer, the term of this patent is extended or adjusted under 35 U.S.C. 154(b) by 331 days.

This patent is subject to a terminal disclaimer.

(21) Appl. No.: 16/866,888

(22) Filed: May 5, 2020

(65) Prior Publication Data

US 2021/0015968 A1 Jan. 21, 2021

Related U.S. Application Data

(63) Continuation of application No. 12/784,950, filed on May 21, 2010, now abandoned.

(60) Provisional application No. 61/182,383, filed on May 29, 2009.

(51) Int. Cl.
*A61L 27/24* (2006.01)
*A61L 27/26* (2006.01)
*A61L 27/56* (2006.01)
*A61L 27/58* (2006.01)

(52) U.S. Cl.
CPC ............... *A61L 27/24* (2013.01); *A61L 27/26* (2013.01); *A61L 27/56* (2013.01); *A61L 27/58* (2013.01); *A61L 2430/32* (2013.01)

(58) Field of Classification Search
CPC .......... A61L 27/24; A61L 27/26; A61L 27/56; A61L 27/58; A61L 2430/32
See application file for complete search history.

(56) References Cited

U.S. PATENT DOCUMENTS

| | | | |
|---|---|---|---|
| 4,778,467 A | 10/1988 | Stensaas et al. | |
| 4,877,029 A | 7/1989 | Valentini et al. | |
| 4,955,893 A | 9/1990 | Yannas et al. | |
| 4,963,146 A | 10/1990 | Li | |
| 5,011,486 A | 4/1991 | Aebischer et al. | |
| 5,019,087 A | 5/1991 | Nichols | |
| 5,026,381 A | 6/1991 | Li | |
| 5,092,871 A | 3/1992 | Aebischer et al. | |
| 5,502,092 A | 3/1996 | Barrows et al. | |
| 5,656,605 A | 8/1997 | Hansson et al. | |
| 5,925,053 A | 7/1999 | Hadlock et al. | |
| 5,948,654 A | 9/1999 | Tranquillo et al. | |
| 5,997,895 A | 12/1999 | Narotam et al. | |
| 6,057,137 A | 5/2000 | Tranquillo et al. | |
| 6,214,021 B1 | 4/2001 | Hadlock et al. | |
| 6,447,701 B1 | 9/2002 | Heschel et al. | |
| 6,461,629 B1 | 10/2002 | Tranquillo et al. | |
| 6,899,873 B2* | 5/2005 | Ma ...................... A61L 27/3878 |
| | | | 435/395 |
| 6,969,523 B1 | 11/2005 | Mattern et al. | |
| 7,198,799 B2 | 4/2007 | Mueller et al. | |
| 2001/0031974 A1 | 10/2001 | Hadlock et al. | |
| 2002/0018799 A1* | 2/2002 | Spector ................... A61L 31/14 |
| | | | 435/368 |
| 2002/0150753 A1 | 10/2002 | Ma et al. | |
| 2003/0176876 A1 | 9/2003 | Chen et al. | |
| 2005/0013844 A1 | 1/2005 | Hadlock et al. | |
| 2011/0129515 A1 | 6/2011 | Archibald | |
| 2015/0073564 A1 | 3/2015 | Valmikinathan et al. | |

OTHER PUBLICATIONS

Rolls et al. PLOS Medicine. 2008; 5(8): 1262-1277. (Year: 2008).*
Paul et al. The Scientific World Journal. 2003; 3: 136-155. (Year: 2003).*
Anonymous. Navy [online]; 2003; downloaded from <URL chrome-extension://efaidnbmnnnibpcajpcglclefindmkaj/https://www.dcms.uscg.mil/Portals/10/CG-1/cg112/docs/pdf/22NAVY030200Eattachment.pdf> on Aug. 26, 2023; 12 pages. (Year: 2003).*
Damink et al. J Mater Sci Mater Med. 1995; 6: 460-472. (Year: 1995).
Paul et al. The Scientific World Journal. 2003; 3: 138-155. (Year: 2003).
Abstract of "Development of a Neural Matrix for Enhanced Peripheral Nerve Repair," Wang, et al., Tissue Engineering Society International, 2003 Annual Meeting, Orlando, Florida.
Harley et al. Cells Tissues Organs.2004; 176(1-3): abstract. (Year: 2004).
Anonymous. Science Learning Hub [online]; 2007; downloaded from <URL https://www.sciencelearn.org.nz/resources/1006-insulation> on Nov. 19, 2018; 6 pages. (Year: 2007).
Sakamoto, "Further Development of Scaffolds for Regeneration of Nerves," Medical Design Briefs, May 2009.
European Search Report issued from corresponding EP Application No. 10163973.0, dated Nov. 26, 2013.
Feb. 2, 2018—International Search Report and Written Opinion of PCT/US2017/064499.
Hattori "Alkali-Treated Collagen Retained the Triple Helical Conformation and the Ligand Activity for the Cell 7 ~dhesioin via a2b1 Integrin" Journal of Biochemistry. vol. 125. pp. 676-784. (1999); Abstract P .. 676 Retrieved from https://www.jstage.jst.go.jp/article/biochemistry1922/125/4/125 4 676/ pdf/-char/en.

* cited by examiner

Primary Examiner — David Browe
(74) Attorney, Agent, or Firm — KDW FIRM PLLC (57) ABSTRACT

The present invention is directed to a nerve regeneration conduit including a resorbable tube having a matrix therein. The matrix is characterized by substantially parallel, axially aligned pores extending the length of the matrix. The matrix is formed by the axial freezing of a slurry having little or no significant radial thermal gradient during the freezing process. The matrix is used to bridge the gap between the severed ends of a nerve and provide a scaffold for nerve regeneration.

14 Claims, 3 Drawing Sheets

SEM Images

Fig. 1    Cross section magnification 15X

Fig. 2  Cross section magnification 100X

Fig. 3   Longitudinal cross section magnification 150X

DEVICES AND METHODS FOR NERVE REGENERATION

This application is a continuation of U.S. patent application Ser. No. 12/784,950 filed on May 21, 2010, which claims the benefit of the filing date of provisional application Ser. No. 61/182,383 filed May 29, 2009, which are both hereby incorporated by reference in their entirety.

FIELD OF THE INVENTION

The present invention relates to the field of mammalian nerve regeneration. Specifically, the present invention relates to methods of making devices useful for nerve regeneration. The present invention further relates to devices and methods that assist in regenerating a severed peripheral nerve by bridging the gap between the ends of the severed peripheral nerve and providing a scaffold to support regrowth of nerve tissue.

BACKGROUND

Nerve regeneration conduits are known. See U.S. Pat. No. 5,019,087. Methods for making nerve regeneration prostheses are also known. See U.S. Pat. No. 4,955,893. However, it is desirable to promote regeneration of nerve tissue to rejoin the ends of severed nerves.

It is therefore an object of the present invention to provide a regenerative scaffold to enhance axon and Schwann cell propagation during the process of peripheral nerve regeneration across nerve gaps greater than allowed by prior entubulation repair techniques. It is also an object of the present invention to provide an apparatus and process that allows the routine manufacture of a biocompatible nerve regeneration conduit comprising a resorbable tube filled with a resorbable matrix having controlled pore size and parallel, axially oriented pore alignment resembling the Schwann cell basal lamina. These and other objects, features, and advantages of the invention or certain embodiments of the invention will be apparent to those skilled in the art from the following disclosure and description of exemplary embodiments.

SUMMARY

Embodiments of the present invention are directed to nerve guides and are further directed to devices and methods for tissue regeneration and, in particular, nerve tissue regeneration using a scaffold of the present invention. According to certain aspects of the present invention, a method is provided in which axial freezing of a suspension or slurry (collectively "slurry") having little or no significant radial thermal gradient followed by freeze drying results in a matrix having a plurality of passages, channels, pathways or pores (collectively, "pores") generally spanning one end of the matrix to the other. In one embodiment of the method, the slurry is thermally insulated to provide it with little or no significant radial thermal gradient during the axial freezing of the slurry.

The configuration of pores produced by methods of the present invention that span one end of the matrix to the other promotes the growth of tissue, and more specifically nerve tissue, into and through the matrix as a whole, as physical obstructions within the pores in the matrix are minimized by the method of the present invention. The pores can be axially-oriented to the extent that the pores allow nerve tissue to grow into and through the matrix. Such pores are directed along the axis of the severed nerve and promote the growth of the nerve tissue into and through the pores of the matrix scaffold.

According to one aspect of the present invention, the matrix allows nerve tissue to grow from opposite ends of the matrix and join together at a point within the matrix, as a characteristic of a plurality of pores is that they span one end of the matrix to the other in an unobstructed manner. In an exemplary embodiment, a severed nerve can be reconnected by interconnecting each severed end of the nerve with the matrix of the present invention and allowing nerve tissue to grow through the matrix from opposite ends until contacting and combining together and, preferably, forming a functioning nerve where it was once severed and nonfunctioning. In this manner, embodiments of the present invention include a prosthesis or implant or scaffold to regenerate damaged nerve fibers that have a gap or distance between the severed ends of the nerve fibers. The prosthesis or implant or scaffold can be made to have different diameters and/or lengths, as desired, for use with different diameter nerve and different gaps or distances between severed nerves.

According to embodiments of the present invention, the step of maintaining the suspension at little or no significant radial thermal gradient while axially freezing the suspension followed by freeze drying optimizes the formation of axially oriented pores. The greater the number and consistency of axially oriented pores within the matrix from one end of the matrix to the other, the greater the ability of the matrix to allow, and even promote, nerve growth therein and therethrough.

According to alternate embodiments of the present invention, the matrix is useful as a device by itself, and can be combined with one or more connectors such as cuffs to allow the joining of the matrix to respective ends of a severed nerve. According to a different embodiment, the matrix can be preformed and then inserted into and housed by a hollow conduit. Alternatively, a suspension can be introduced into a conduct which is maintained at little or no significant radial thermal gradient and then the suspension can be axially frozen followed by freeze drying to form the matrix within the conduit. In either embodiment, the conduit housing the matrix can likewise be combined with one or more connectors, such as cuffs to allow the joining of the matrix to respective ends of a severed nerve. Still alternatively, the end portions of the conduit may be hollow, may lack matrix or otherwise may extend beyond the matrix therein to allow the severed end of a nerve to be inserted into the conduit in a manner to contact the matrix and allow nerve growth therein.

DETAILED DESCRIPTION OF CERTAIN EXEMPLARY EMBODIMENTS

Embodiments of the present invention are based on the discovery of a device and method that produces axially aligned pores in a matrix using a slurry having little or no significant radial thermal gradient during axial freezing of the slurry. In one embodiment, the slurry is thermally insulated to maintain little or no significant radial thermal gradient during axial freezing. The term "little or no significant radial thermal gradient" means no detectable thermal gradient in the radial direction of the slurry or at the very least any thermal gradient that exists does not adversely affect the formation of axially aligned pores. For purposes of exemplary embodiments of the present invention, little or no significant radial thermal gradient is achieved by insulating the slurry during axial freezing of the slurry. Without being bound by any scientific theory, axial freezing of the slurry having little or no significant radial thermal gradient is believed to produce axially aligned ice crystals along the length of the slurry. Freeze drying removes the crystals and leaves behind a matrix having axially aligned pores.

In accordance with a first aspect of the invention, the slurry used to form the matrix includes materials known to those of skill in the art used to form such matrices. The materials include biocompatible and/or bioresorbable materials that can form a liquid slurry or suspension. Such materials include collagen, laminin, fibronectin, merosin, hyaluronic acid, chitin, chitosan, keratin, polyglycolic acid, polylactic acid, cellulose and the like. The materials can be used alone or in combination with each other. It is to be understood that the list of materials is not exhaustive and that one of skill in the art will readily identify other materials useful to make slurries based on the present disclosure. In certain exemplary embodiments, the matrix is formed from collagen. Collagen is a fibrous protein and constitutes the major protein component of skin, bone, tendon, ligament, cartilage, basement membrane and other forms of connective tissue. Collagen is biodegradable, and when implanted in the body, is absorbed at a rate that can be controlled by the degree of intra- or intermolecular cross-linking imparted to the collagen molecule by chemical or physical treatment. Thus upon implantation, the collagen matrix can be designed to be absorbed as the tissue grows into the matrix, such as when nerve tissue regenerates and grows into the matrix.

In certain exemplary embodiments, the matrix includes collagen and at least one glycosaminoglycan. Exemplary glycosaminoglycans include chondroitin sulfate, dermatan sulfate, keratin sulfate, hyaluronic acid, and the like. The glycosaminoglycans can be used alone or in combination with each other. It is to be understood that the list of glycosaminoglycans is not exhaustive and that one of skill in the art will readily identify other materials useful to make slurries based on the present disclosure. In certain exemplary embodiments, the collagen and the glycosaminoglycan are cross-linked. Cross-linking can be achieved by heating under vacuum or by treatment with chemical cross-linking agents, e.g., glutaraldehyde, formaldehyde, chromium sulfate, carbodiimide, adipyl dichloride, and the like.

The materials to form the matrix are combined with a liquid to form a slurry which is then introduced into a mold to form a matrix of a desired shape. Suitable liquids within the scope of the invention should be capable of being removed by freeze drying and include water, and aqueous fluids containing alcohol, acetic acid and the like. The liquids can be used alone or in combination with each other. It is to be understood that the list of liquids is not exhaustive and that one of skill in the art will readily identify other materials useful to make slurries based on the present disclosure. Methods of freeze drying materials that contain liquids such as water are known to those of skill in the art.

Other materials can be included into or otherwise form the slurry and therefore can be incorporated into the matrix as desired. Such other materials include drugs, growth factors, extracellular matrix components, fibrous materials and the like. The other materials can be used alone or in combination with each other. It is to be understood that the list of other materials is not exhaustive and that one of skill in the art will readily identify still other materials based on the present disclosure.

It is to be understood that molds of any desired shape can be used in the present invention based upon the principles disclosed herein and for use where it is desired that tissue grow into the pores of the matrix. Particular molds can be used to produce various desired matrix shapes including cylinders, rectangles, spheres, sheets and other desired shapes and can even be in the same general shape as wound sites or tissue defects so that the matrix can be fit to the particular wound site or tissue defect. Although the matrices of the present invention can be used to regenerate and connect severed nerves, the matrices also have other uses where reconnecting severed or broken tissue or rebuilding damaged tissue through tissue regeneration would be advantageous. Such applications include regeneration of tendon, articular cartilage, bone, corticospinal tracts, and other linearly aligned structures.

An exemplary mold can produce a single matrix or a mold may be capable of producing a plurality of matrices, such as where the mold includes a plurality of chambers of desired design into which the slurry can be introduced and then subject to axial freezing. Such a mold contemplates commercial manufacture of the matrices of the present invention where it is desired to mass produce such matrices in a batch format. Individual chambers within a mold are insulated so the slurry therein has little or no significant thermal gradient during axial freezing. Each individual chamber can include an insulating material therein surrounding the chamber or the entire mold can be formed from an insulating material thereby insulating the slurry in the individual chambers. Suitable insulating materials include STYROFOAM, AEROGEL and the like.

According to an additional exemplary embodiment, the matrix can be used by itself or it can be preformed and then inserted into a hollow conduit for use as a prosthesis. Alternatively, the matrix can be formed directly inside a hollow conduit. According to this embodiment, a slurry is placed into a hollow conduit which is insulated. The axial freezing process and freeze drying process takes place to form the matrix within the conduit. The conduit containing the matrix is then used as a prosthetic device to connect severed tissue. In one embodiment, the conduit is biodegradable or bioresorbable. An exemplary period of time for biodegradability or bioresorbability is within about 1 to about 3 months. An exemplary embodiment is a resorbable collagen tube, as is commercially available under the brand name NEURAGEN from Integra LifeSciences Corporation, Plainsboro, N.J. Methods for making certain exemplary embodiments of the resorbable tube are disclosed in U.S. Pat. No. 5,019,087, which is incorporated herein by reference in its entirety.

In certain exemplary embodiments, the collagen in the resorbable tube is Type I collagen, and the tube further comprises a laminin-containing material. Laminin is a glycoprotein that is an abundant component of all basement membranes. As used herein, the phrase "laminin-containing material" is meant to include purified laminin itself or a material which contains laminin and other basement membrane components and is capable of forming a dispersion from which the resorbable tubes are made. Materials which contain laminin include basement membranes, human placenta, and an extract of a mouse sarcoma known in the art as Matrigel. In certain exemplary embodiments, the amount of Type I collagen that is combined with the laminin present in the laminin-containing material on a dry weight basis is in the ratio of about 90:10 to 40:60. In certain exemplary embodiments other optional additives which may aid in the nerve regeneration may also be present in the resorbable tube in addition to collagen, for example, heparin, heparan sulfate proteoglycan, glycosaminoglycans such as hyaluronic acid, chondroitin sulfate and others, growth hormones such as epidermal growth factor (EGF), nerve growth factor, glycoproteins such as fibronectin, and the like. The glycosaminoglycans can be used alone or in combination with each other. It is to be understood that the list of optional additives is not exhaustive and that one of skill in the art will readily identify other optional additives useful in the present invention based on the present disclosure.

In certain exemplary embodiments, the resorbable tube may be cross-linked. This can be done with chromium sulfate, formaldehyde, glutaraldehyde, carbodiimide, adipyl dichloride, and the like. The rate at which the resorbable tube of the present invention is resorbed in vivo in a mammal is dependent on the degree of cross-linking. Factors controlling the extent of crosslinking are the type and concentration of the cross-linking agent, the pH, and the temperature of incubation. In certain exemplary embodiments, the nerve regeneration conduits of the present invention are cross-linked to such an extent that they are completely resorbed within about 1 to about 3 months.

In certain exemplary embodiments, the resorbable tube has a length of about 1 cm to about 15 cm, and an inner diameter in the range of from about 1 mm to about 1.5 cm. The length of the resorbable tube may vary with the length of the nerve gap to be bridged, and the inner diameter may vary with the diameter of the nerve. In certain exemplary embodiments, the resorbable tube has a length of about 2 cm to about 10 cm, e.g., a length of about 2 cm to about 4 cm, a length of about 3 cm to about 7 cm. In certain exemplary embodiments, the inner diameter of the resorbable tube is in the range from about 1 mm to about 15 mm, e.g., from about 1.5 mm to about 10 mm. The wall thickness of the resorbable tube represents a balance between desired permeability and enough compressive strength to prevent collapse. Preferably, the tubes are made as thin as possible while still withstanding suturing and collapse when used in vivo. In certain exemplary embodiments, the resorbable tube has a wall thickness in the range of from about 0.2 mm to about 1.2 mm, e.g. about 0.1 mm to about 0.8 mm. In certain exemplary embodiments, the resorbable tube is less porous than the matrix.

According to exemplary embodiments of the present invention, the slurry is subject to axial freezing. A cooling gradient is generated in the axial direction of the slurry when in the mold by rapid heat transfer from the slurry to a cooling medium, and where the cooling gradient has substantially no radial component. Cooling in this manner forms substantially parallel, axially aligned ice crystals in the slurry. According to certain exemplary embodiments, a heat sink at one end of the slurry causes heat to be drawn out of the slurry in an axial manner. A heat sink in accordance with the principles of the present invention includes a thermally conducting plug that contacts the slurry and in turn is in contact with a cooling medium. The thermally conducting plug acts as a heat sink, as well as sealing off one end of the tube where slurry is added to the tube. The plug can be made of any material that has high thermal conductivity, such as metals and metal alloys (e.g., brass, steel, copper, zinc, nickel, and aluminum, among others). The thermally conducting plug can be inserted into the mold that contains the slurry, thereby contacting the slurry. According to one embodiment, the thermally conducting plug can serve as a stop within the mold, such as when the mold shape is a cylinder and is positioned perpendicular to the cooling medium with the thermally conducting plug directly contacting the cooling medium.

Suitable cooling media include any solid or liquid media capable of freezing the liquid slurry, for example, a cooling medium that maintains a temperature between about −78° C. and about −196° C. Certain exemplary embodiments of the method of the invention include the step of contacting the thermally conducting plug with a cooling medium to provide a cooling gradient in the axial direction of the insulated tube. The cooling medium may be at least one of liquid nitrogen, dry ice, an isopropanol/dry ice mixture, and silicone oil cooled by liquid nitrogen, and the like, whether directly contacting the thermally conducting plug or indirectly through a different media such as a cold plate and the like. The cooling media can be used alone or in combination with each other. It is to be understood that the list of cooling media is not exhaustive and that one of skill in the art will readily identify other cooling media useful to freeze slurries based on the present disclosure. Once the slurry, such as an aqueous slurry, is completely frozen, the tube filled with frozen aqueous slurry is dried under vacuum (e.g., by freeze drying or lyophilizing) to produce a nerve regeneration conduit of the present invention.

As heat is drawn out of the slurry in an axial manner by the heat sink, freezing of the slurry proceeds along the length of the slurry from the end of the slurry proximal to the heat sink to the distal end of the slurry. The slurry, whether directly in a mold or in a conduit, is thermally insulated with little or no significant thermal gradient to significantly affect freezing of the slurry at the point of contact of the slurry with the wall of the mold or the conduit.

Axial freezing combined with thermal insulation followed by freeze drying produces substantially parallel, axially aligned pores extending the length of the matrix. Ice crystal formation occurs along the gradient of cooling. If the temperature gradient is uniform through a volume of space, and each plane in the volume perpendicular to the direction of the temperature gradient is of a uniform temperature, and the gradient is sufficient to propagate ice crystal formation throughout the length of the gradient, then the formation of ice crystals in such a defined region will extend through the region in a manner aligned to the direction of the gradient. Thus, the ice crystals will be substantially parallel to the gradient and substantially parallel to each other. In certain exemplary embodiments of an aqueous slurry and a tubular mold, this axial cooling gradient is achieved by thermally insulating the aqueous slurry or the walls of the tube containing the aqueous slurry to be frozen. Insulating the tube can be done with any material that prevents heat transfer through the wall of the tube. This substantially eliminates any radial component in the cooling gradient, providing a uniform axial cooling gradient. Subsequent freeze drying or lyophilizing of the frozen slurry in the tube results in a matrix having open channels comprising substantially parallel, axially oriented pores The pores have an average diameter of about 10 μm to about 300 μm, about 50 μm to about 250 μm, or about 100 μm to about 200 μm. The matrix can be any length depending upon the desired application, however, suitable lengths include from about 2 cm to about 20 cm, from about 3 cm to about 15 cm or from about 5 cm to about 10 cm and ranges therebetween.

In accordance with a certain aspect of the invention, the matrix of the present invention is used to promote in vivo regeneration of a severed mammalian nerve so as to bridge a gap between a first end and a second end of the severed nerve. The matrix can be included within a conduit having a first end and a second end. The matrix may be flush with the first end and second end of the conduit or it may be recessed within one or both ends of the conduit. Alternatively, the matrix may extend beyond one or both ends of the conduit, if desired. According to one embodiment, connectors may be used to connect the conduit containing the matrix, or the matrix alone, to the severed end of a nerve. Suitable connectors within the scope of the present invention overlap the conduit and the nerve and include wraps or cuffs with or without sutures or any other suitable connector design that can be used to connect the conduit or matrix to the severed end of a nerve.

One particular example of a connector is a collagen sheet or wrap that can be placed or wrapped around the nerve and the conduit and then secured in place, such as by using sutures. One such collagen sheet or wrap is marketed under the NEURAWRAP mark from Integra LifeSciences Corporation, Plainsboro, N.J. Such sheets or wraps can be in a cylindrical form having a longitudinal slit where opposing ends of the wrap can be pulled apart, the nerve inserted and then the wrap can rebound into a cylindrical position around the nerve. Such sheets or wraps can be made from biodegradable or bioerodable materials such as collagen, laminin, fibronectin, merosin, hyaluronic acid, chitin, chitosan, keratin, polyglycolic acid, polylactic acid, cellulose and the like. The materials can be used alone or in combination with each other. It is to be understood that the list of materials is not exhaustive and that one of skill in the art will readily identify other materials useful to make sheets or wraps based on the present disclosure.

Where the matrix is flush with an end of the conduit, another suitable connector is a cuff having a first open end and a second open end. The cuff has an outer diameter larger than the outer diameter of the conduit. The cuff conforms to the outer shape of the conduit. For example, if the conduit is tubular or cylindrical, the cuff will be a tubular or cylindrical cuff. A cuff is placed onto the outer end of the conduit with a portion of the cuff extending over the end of the conduit. The first end of the severed nerve is inserted into the cuff extension and is brought into contact with the first end of the matrix to form a first junction between the severed nerve and the conduit. The nerve, cuff and conduit are all secured in place at this first junction according to methods known to those skilled in the art, such as suturing. The second end of the severed nerve is brought into contact with the second end of the matrix to form a second junction between the severed nerve and the conduit. This junction may also be secured in place with a cuff as described above. Cuffs according to embodiments of the present invention can be formed from various materials including collagen laminin, fibronectin, merosin, hyaluronic acid, chitin, chitosan, keratin, polyglycolic acid, polylactic acid, cellulose and the like. The materials can be used alone or in combination with each other. It is to be understood that the list of materials is not exhaustive and that one of skill in the art will readily identify other materials useful to make cuffs based on the present disclosure. Suitable commercially available cuffs include resorbable collagen tubes having a length sufficient for a cuff, as are commercially available under the brand name NEURAGEN from Integra LifeSciences Corporation, Plainsboro, N.J. Methods for making certain exemplary embodiments of the resorbable tube are disclosed in U.S. Pat. No. 5,019,087, which is incorporated herein by reference in its entirety.

If, according to an exemplary embodiment, the matrix is recessed within one or both ends of the conduit, i.e. the end of the conduit extends past the matrix therein, the severed nerve is introduced into the conduit until it contacts the matrix to form a junction and the nerve is secured in place within the conduit using methods known to those skilled in the art, such as suturing. No connector such as a sheet, wrap or cuff is required with this exemplary embodiment, although a sheet, wrap or cuff could still be used if desired.

In certain exemplary embodiments where the ends of the conduit, such as a resorbable tube, extend past matrix therein, a distance into each end of the tube is unfilled with the slurry to form the matrix, or alternatively, matrix is removed from within the tube, or still alternatively, matrix of length shorter than the tube is inserted into the tube. Methods for making an embodiment where the matrix is formed within the tube include plugging the bottom of the tube with a plug that extends a distance into the tube, followed by filling the tube with slurry up to a desired point, which can include the end of the tube or a location before the end of the tube thereby allowing the end of the tube to extend past the matrix. These embodiments allow insertion of a severed nerve end into a hollow end of the resorbable tube and contact of the nerve end with the matrix inside the tube. The nerve end inside the hollow end of the resorbable tube may then be sutured to the tube.

In a certain exemplary embodiment, nerve regeneration conduits according to the present invention include a resorbable tube having a matrix of controlled pore size and parallel structure that mimics Schwann cell basal lamina, which significantly enhances Schwann cell migration and axon regeneration through the conduit. Schwann cells are non-neuronal cellular elements that provide structural support and insulation to axons. Thus, by using the conduits of the present invention in a manner such that the respective ends of a severed nerve are brought into contact with each end of the conduit fashioned from a resorbable tube filled with a matrix having substantially parallel, axially aligned pores extending the length of the matrix, greater numbers of regenerating axons are stimulated, many of which become mylenated, a substantial increase in the initial rate of the outgrowth of fibers and mylenated axons is produced, and the regenerating axons are able to span the gap between the severed nerve by growing through the matrix.

The matrices of the present invention promote parallel axial alignment of regenerated nerve tissue accompanied by a large number of Schwann cells. The axial oriented pores of the matrices of the present invention promote peripheral nerve regeneration that is axially aligned to the direction of the resorbable matrix, with the oriented pores being substantially parallel to each other along the entire length of the desired route of nerve regeneration. For example, an axon entering a pore of the nerve regeneration conduit of the present invention should exit the opposite end of the conduit at substantially the same relative position.

The pore size and parallel alignment in the matrix are intended to resemble the Schwann cell basal lamina so as to encourage axon growth. In certain exemplary embodiments, the population of pores in the matrix have an average diameter of about 10 µm to about 300 µm. In an alternate embodiment, the population of the pores in the matrix have an average diameter from about 40 µm to about 180 µm or an average diameter from about 80 µm to about 120 µm.

Certain exemplary embodiments of the present invention are directed to a system including an apparatus used to freeze the slurries of the present invention. The apparatus includes a vessel filled with a heat transfer fluid and including a coil through which coolant flows. The temperature of the fluid is monitored and controlled at a desired temperature. A collagen tube of desired size is fitted at one end with a heat sink such as a copper rod and the collagen tube is inserted into PVC tubing. The PVC tubing with the collagen tube and copper rod is housed in insulating material with the heat sink protruding beyond the insulating material. According to one method of the present invention, a slurry is poured into the collagen tube and the heat sink is contacted to the heat transfer fluid, i.e. liquid cooling medium, with the insulating material acting as a float, as the insulating material is buoyant when placed in the liquid cooling material. In this embodiment the collagen tube is held in a substantially vertical position within the insulating material with the heat sink contacting the liquid cooling material. The slurry is allowed to freeze and the frozen slurry is then lyophilized to form a matrix. The matrix may then be further processed such as by undergoing crosslinking. The matrix may then be packaged and sterilized according to methods known to those of skill in the art.

Certain other exemplary embodiments of the method of the present invention include surrounding a bioresorbable or biodegradable tube have a thermally conducting plug at one end with a material that thermally insulates the tube and the slurry within so that there is substantially no thermal gradient in the radial direction of the tube. As a non-limiting example, the tube may be inserted into a block of polymer foam or other insulating material, such as STYROFOAM or AEROGEL, so that the plug protrudes from the bottom of the block and the open end of the tube is flush with the top of the block. The block of polymer foam serves as a thermal insulator to prevent heat transfer through the walls of the tube. Thus, any thermal gradient in the tube will have substantially no radial component. The polymer foam may comprise one or more of the following insulating materials: polystyrene, polyurethane, polyethylene, ceramic and silicone, and the like. The insulating media can be used alone or in combination with each other. It is to be understood that the list of insulating media is not exhaustive and that one of skill in the art will readily identify other insulating media based on the present disclosure. Alternatively, the tube may be insulated with any other material that substantially prevents heat transfer, for example, a vacuum- or gas-filled jacket or flask.

In certain exemplary embodiments, the method of using matrices, especially matrix-filled conduits, includes the steps of bringing the respective ends of the severed nerve into contact with each end of the nerve regeneration conduit of the present invention, which conduit is equal to or longer than the gap to be bridged so that no tension is placed upon the severed nerve. Both the distal and proximal nerve ends are partially inserted into the ends of the resorbable tube, optionally until the nerve ends contact the matrix filling the tube, and sutured over their perineurium.

Use of the nerve regeneration conduit of the present invention promotes nerve regeneration across nerve gaps of up to 15 cm. In certain exemplary embodiments, the nerve regeneration conduit promotes regeneration across nerve gaps of about 2 cm to about 10 cm, e.g., about 2 cm to about 4 cm, about 3 cm to about 7 cm. Nerve diameters that can be accommodated by the nerve regeneration conduit of the present invention range from about 1 mm to about 1.5 cm, e.g., about 2 mm and about 7 mm, about 3 mm to about 10 mm.

EXAMPLES

The following examples are specific embodiments of the present invention but are not intended to limit it.

Example 1

A resorbable tube having a porous matrix according to the present invention was achieved by highly controlled freezing and insulation of an aqueous dispersion of collagen, followed by freeze drying. The pore structure and orientation of the matrix formed by the process of the invention was examined by taking scanning electron microscope (SEM) images of transverse and longitudinal cross-sections of the resulting matrix.

Specifically, a brass bolt was inserted into one end of a NEUROGEN collagen tube to both plug the tube and act as a heat sink. The tube was then inserted into a polystyrene foam block so that the bolt protruded from the bottom face of the block, and the open end of the tube was flush with the top face of the block. An aqueous collagen slurry was prepared according to the method described in U.S. Pat. No. 6,969,523 hereby incorporated by reference herein in its entirety. Suitable methods to prepare a slurry useful in the present invention are also described in U.S. Pat. No. 5,997,895 hereby incorporated herein by reference in its entirety. The tube was filled with the aqueous collagen slurry, and the polystyrene foam block was floated with the bolt on the bottom face of the block immersed in a bath of silicone oil that had been cooled by liquid nitrogen. The collagen slurry in the tube froze entirely within about 30 minutes. The tube with the frozen slurry was then placed in a pre-cooled lyophilizer and freeze dried under vacuum.

Figure 1:
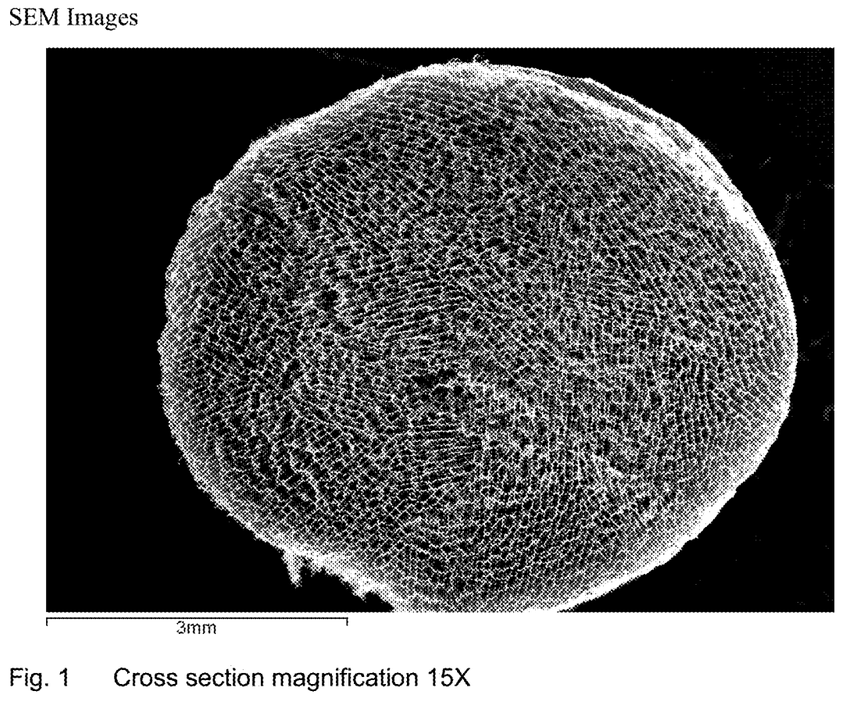
FIG. 1 is a scanning electron micrograph at 15× of a cross-section of a matrix produced by the method of the present invention.
Figure 2:
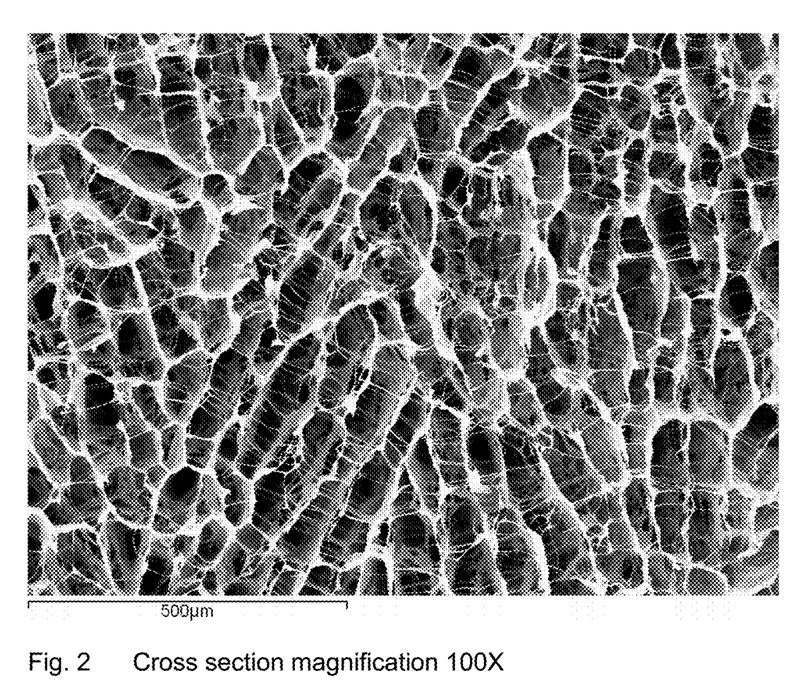
FIG. 2 is a scanning electron micrograph at 100× of a cross-section of a matrix produced by the method of the present invention.
Figure 3:
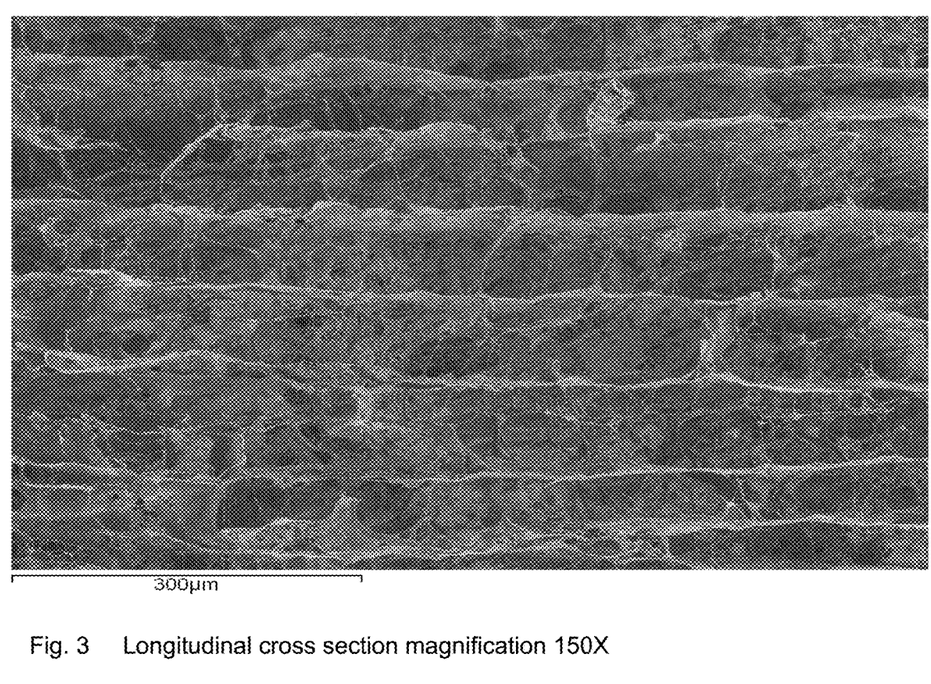
FIG. 3 is a scanning electron micrograph at 150× of a longitudinal cross section of a matrix produced by the method of the present invention.

FIG. 1 is a scanning electron micrograph at 15× of a cross-section of a matrix produced by the method of the present invention. FIG. 2 shows the matrix at 100×. FIG. 3 is a scanning electron micrograph at 150× of a longitudinal cross section of a matrix produced by the method of the present invention.

FIG. 1-FIG. 3 show substantially uniform pore structures where the pores are substantially parallel, axially aligned, and extending the length of the matrix. The pores are believed to mimic the highly axially oriented pore structure of Schwann cell basal lamina.

Example 2

A 4.5 cm long by 7 mm diameter tube was provided having walls formed from collagen and a laminin-containing material according to the process of U.S. Pat. No. 5,019,087. A copper rod was inserted into one end of the tube to both plug the tube and act as a heat sink. The tube was then inserted into a polystyrene foam block so that the copper rod protruded from the bottom face of the block, and the open end of the tube was flush with the top face of the block. The tube was filled with aqueous slurry of collagen and a glycosaminoglycan, and the polystyrene foam block was floated with the copper rod on the bottom face of the block immersed in a bath of liquid nitrogen. The collagen slurry in the tube froze entirely within 12 minutes. The tube with the frozen slurry was then placed in a pre-cooled lyophilizer and freeze dried under vacuum. The resulting porous matrix inside the tube was examined in both cross-section and longitudinal section which showed a matrix having substantially parallel, axially oriented pores extending the length of the matrix. Average pore diameter was between about 165 μm to about 180 μm. The openness of the parallel pores was tested by inducing charged fluorescent beads to migrate through the porous matrix under the influence of a voltage gradient. The majority of the charged fluorescent beads were able to pass through the porous matrix from one end to the other, thus demonstrating that the majority of the parallel, axially aligned pores were open and extended along the length of the matrix.

Example 3

A tube was provided having walls formed from collagen and a laminin-containing material according to the process of U.S. Pat. No. 5,019,087. A copper rod was inserted into one end of the tube to both plug the tube and act as a heat sink. The tube was then inserted into a polystyrene foam block so that the copper rod protruded from the bottom face of the block, and the open end of the tube was flush with the top face of the block. The tube was filled with an aqueous slurry of collagen and a glycosaminoglycan made according to the method described in Example 1, and the polystyrene foam block was placed in a Styrofoam box partially-filled with dry ice so that the copper rod directly contacted the dry ice. The collagen slurry in the tube froze entirely within 1 hour 30 minutes. The tube with the frozen slurry was then placed in a pre-cooled lyophilizer and freeze dried under vacuum. The resulting porous matrix inside the tube was examined in both cross-section and longitudinal section which showed a matrix having substantially parallel, axially oriented pores extending the length of the matrix. Average pore diameter was about 361 μm. The average pore diameter resulting from the freezing method of this Example is notably larger than the average pore size resulting from the freezing method of Example 2, as it is believed that a slower freezing time allows for growth of larger ice crystals, which results in larger pores.

Example 4

An average freezing point of −22.03° C. was experimentally determined for an aqueous slurry of collagen and glycosaminoglycan by freezing five samples according to the table below.

| Sample | Weight (mg) | Freezing Temperature (° C.) |
|---|---|---|
| 1 | 15.0 | −15.95 |
| 2 | 21.3 | −24.04 |
| 3 | 33.1 | −24.14 |
| 4 | 31.4 | −24.07 |
| 5 | 22.6 | −21.94 |

Given the benefit of the above disclosure and description of exemplary embodiments, it will be apparent to those skilled in the art that numerous alternative and different embodiments are possible in keeping with the general principles of the invention disclosed here. Those skilled in this art will recognize that all such various modifications and alternative embodiments are within the true scope and spirit of the invention. The appended claims are intended to cover all such modifications and alternative embodiments. It should be understood that the use of a singular indefinite or definite article (e.g., "a," "an," "the," etc.) in this disclosure and in the following claims follows the traditional approach in patents of meaning "at least one" unless in a particular instance it is clear from context that the term is intended in that particular instance to mean specifically one and only one. Likewise, the term "comprising" is open ended, not excluding additional items, features, components, etc.

What is claimed is:

1. A method for making nerve regeneration conduits for nerve regeneration, the method comprising:
    providing a mold having a plurality of chambers formed therein, wherein the mold is formed from a thermal insulating material, such that each of the plurality of chambers in the mold is insulated from all other chambers of the plurality of chambers in the mold;
    providing a collagen conduit within each of the plurality of chambers in the mold, wherein the collagen conduit has first and second open ends and is resorbable;
    holding, using the mold, each of the collagen conduits in a vertical position within a corresponding one of the plurality of chambers of the mold;
    placing a heat sink at a first end of each of the plurality of chambers of the mold, such that the collagen conduit is held vertically relative to the heat sink;
    introducing a liquid slurry into each of the collagen conduits while each of the collagen conduits is held in the vertical position within the mold, such that the liquid slurry contacts the heat sink, wherein the liquid slurry comprises collagen, chondroitin sulfate, and water;
    conductively transferring heat, using the heat sink, from the liquid slurry in each of the plurality of chambers of the mold to axially freeze the liquid slurry along a length of each of the collagen conduits, such that the liquid slurry is progressively frozen, starting from the first open end, which is proximal to the heat sink, to the second open end of the collagen conduit, such that a frozen slurry is formed from the liquid slurry, the frozen slurry having ice crystals that are parallel to, and axially aligned with, each other;
    lyophilizing the frozen slurry to remove the ice crystals from the frozen slurry, thereby forming a matrix that has pores that are parallel to, and axially-aligned with, each other, wherein the pores span from a first end of the matrix to a second end of the matrix within the collagen conduit; and
    cross-linking each of the collagen conduits and the matrix contained therein.

2. The method of claim 1, wherein the pores each have an average diameter of about 10 μm to about 300 μm.

3. The method of claim 1, wherein the pores each have an average diameter of about 50 μm to about 250 μm.

4. The method of claim 1, wherein the pores each have an average diameter of about 100 μm to about 200 μm.

5. The method of claim 1, wherein:
    conductively transferring heat from the liquid slurry comprises using the heat sink to transfer heat from the liquid slurry to a cooling medium; and
    the heat sink comprises a thermally conductive plug or pole that is arranged to contact the liquid slurry and the cooling medium.

6. The method of claim 5, wherein the cooling medium is a solid or liquid medium capable of freezing the liquid slurry.

7. The method of claim 1, wherein, in each of the nerve regeneration conduits:
    the collagen conduit is cylindrical; and
    the matrix is cylindrical.

8. The method of claim 1, wherein, in each of the nerve regeneration conduits:
the collagen conduit has a length from about 1 cm to about 15 cm; and
the matrix has a length from about 1 cm to about 15 cm.

9. The method of claim 1, wherein the collagen conduit in each of the nerve regeneration conduits has an inner diameter that is in a range from about 1 mm to about 15 mm.

10. The method of claim 1, wherein cross-linking the collagen conduit and the matrix comprises treating the collagen conduit and the matrix with a chemical crosslinking agent.

11. The method of claim 10, wherein the chemical cross-linking agent is glutaraldehyde, chromium sulfate, carbodiimide, or adipyl dichloride.

12. The method of claim 1, wherein cross-linking the collagen conduit and the matrix causes the collagen conduit and the matrix to be completely resorbed in a mammal into which the collagen conduit and the matrix are implanted within about 1 month to about 3 months.

13. The method of claim 1, wherein cross-linking the collagen conduit and the matrix comprises heating the collagen conduit and the matrix while a vacuum is applied thereto.

14. The method of claim 10, wherein the chemical cross-linking agent is formaldehyde.

\* \* \* \* \*